(12) United States Patent
Rowe

(10) Patent No.: US 8,480,230 B2
(45) Date of Patent: Jul. 9, 2013

(54) PHANTOM FOR RENDERING BIOLOGICAL TISSUE REGIONS

(75) Inventor: T. Scott Rowe, Dana Point, CA (US)

(73) Assignee: Rowe Technical Design, Inc., Dana Point, CA (US)

( * ) Notice: Subject to any disclaimer, the term of this patent is extended or adjusted under 35 U.S.C. 154(b) by 35 days.

(21) Appl. No.: 13/013,590

(22) Filed: Jan. 25, 2011

(65) Prior Publication Data

US 2011/0181836 A1 Jul. 28, 2011

Related U.S. Application Data

(60) Provisional application No. 61/298,113, filed on Jan. 25, 2010, provisional application No. 61/425,124, filed on Dec. 20, 2010.

(51) Int. Cl.
*A61B 3/10* (2006.01)
*A61B 3/14* (2006.01)

(52) U.S. Cl.
USPC .......................................... 351/205; 351/206

(58) Field of Classification Search
USPC .................................................. 351/200–246
See application file for complete search history.

(56) References Cited

U.S. PATENT DOCUMENTS 7,547,102 B2 * 6/2009 Dai ............................... 351/205
7,909,465 B2 * 3/2011 Ho et al. ....................... 351/221

2011/0134390 A1 6/2011 Schmid et al.
2011/0170059 A1 * 7/2011 Ehrmann et al. ............ 351/205
2011/0291321 A1 12/2011 Chan et al.

OTHER PUBLICATIONS

De Bruin, D.M. et al., "Optical phantoms of varying geometry based on thin building blocks with controlled optical properties", *J. Biomed. Opt.*, Mar./Apr. 2010, vol. 15, Issue 2, pp. 025001-1 to 025001-10.
Passos, D. et al., "Tissue phantom for optical diagnostics based on a suspension of microspheres with a fractal size distribution", *J. Biomed. Opt.*, Nov./Dec. 2005, vol. 10, Issue 6, pp. 064036-1 to 064036-11.
Zawadzki, R. et al., "Progress report on building an anatomically correct solid eye model with volumetric representation of retinal morphology", International Society of Imaging the Eye (ISIE) 7th Annual Meeting, held in conjunction with the Association for Research in Vision and Ophthalmology (ARVO) Annual Meeting, May 1, 2010, Poster Presentation.
Zawadzki, R. et al., "Toward an anatomically correct solid eye model with volumetric representation of retinal morphology", SPIE BIOS Conference Poster 7550-89, Jan. 26, 2010, San Francisco, CA.

* cited by examiner

*Primary Examiner* — Mohammed Hasan
(74) *Attorney, Agent, or Firm* — Knobbe, Martens, Olson & Bear LLP

(57) ABSTRACT

Models of anatomical parts and methods utilizing and fabricating such anatomical models are provided. The model can include an assembly of one or more optically transmissive media having a first portion and a second portion. The one or more optically transmissive media can be configured to provide similar optical properties as that between two regions of the anatomical part. For example, in an example eye model, the two regions can be a corneal surface and/or retina regions of an eye. A rendered retina can be formed in the second portion of the assembly and can be representative of the retina of the eye. The rendered retina can have one or more features associated with the retina of the eye.

17 Claims, 18 Drawing Sheets

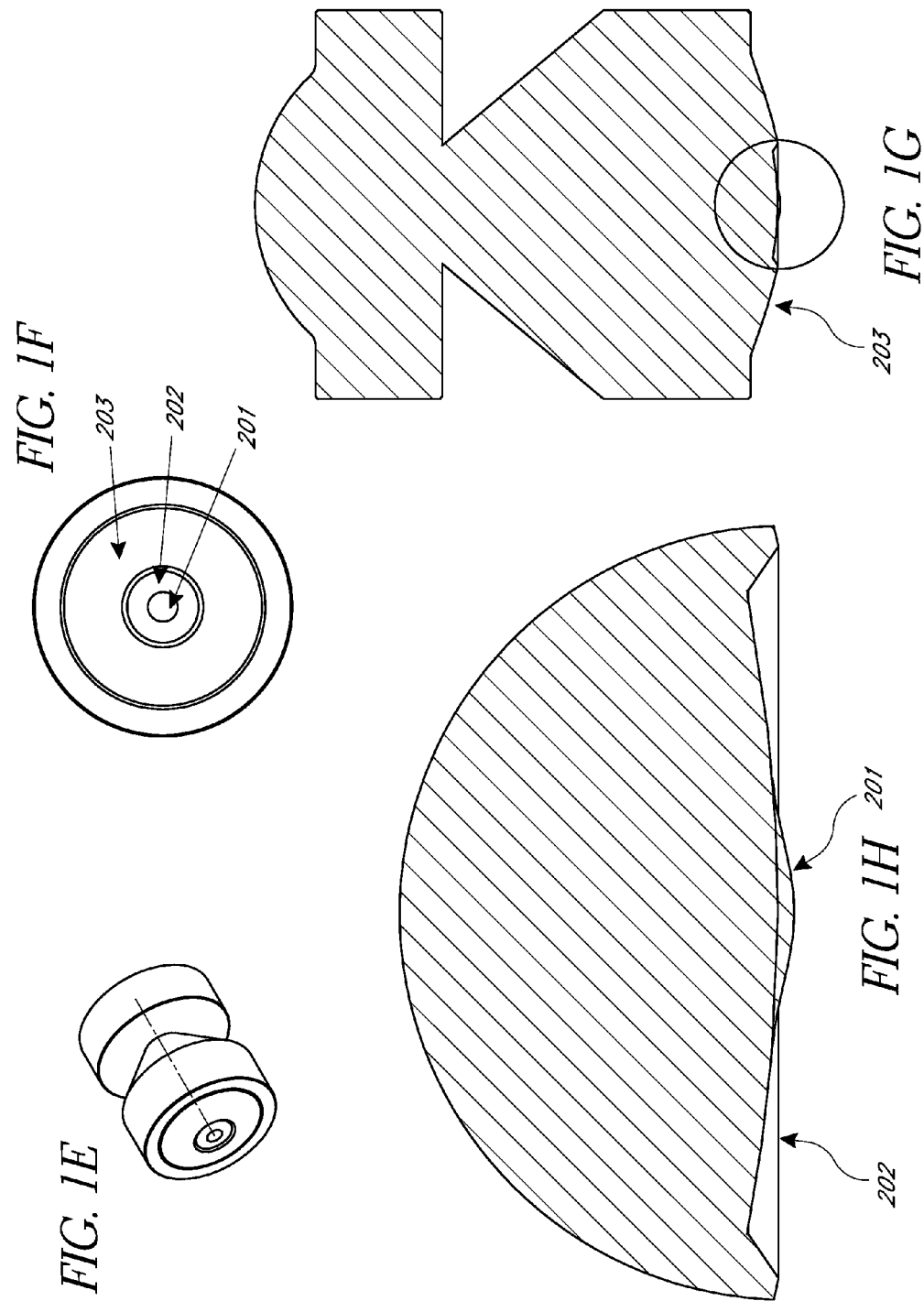

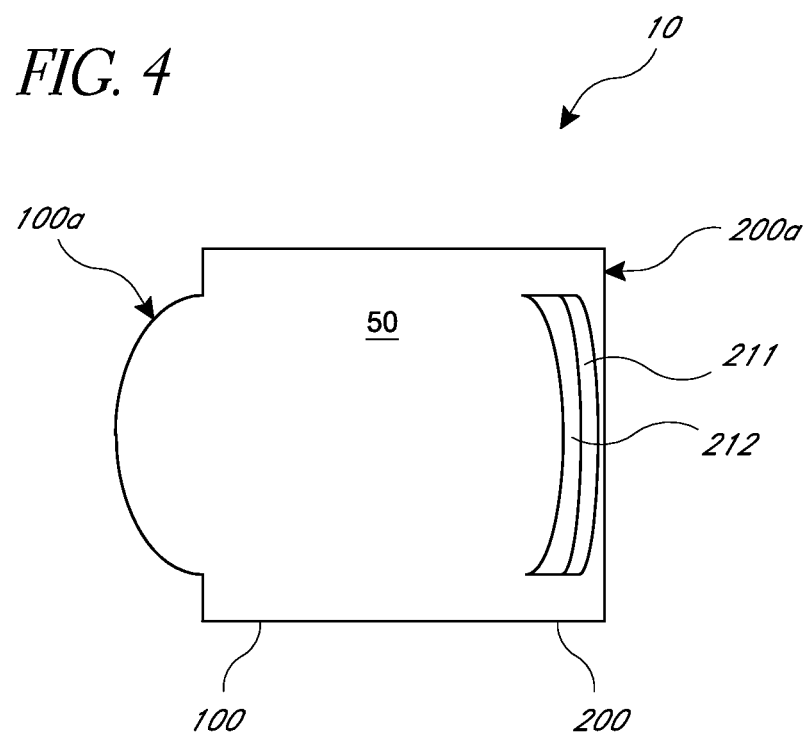

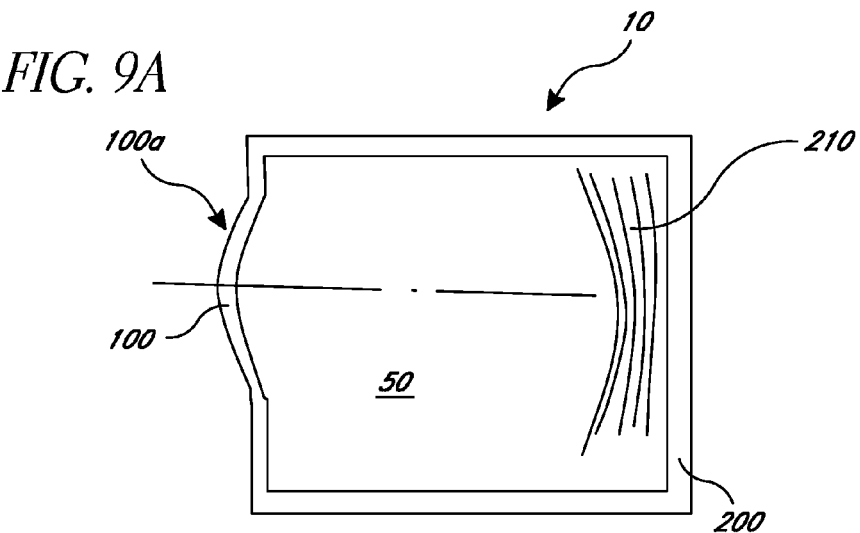
FIG. 9A
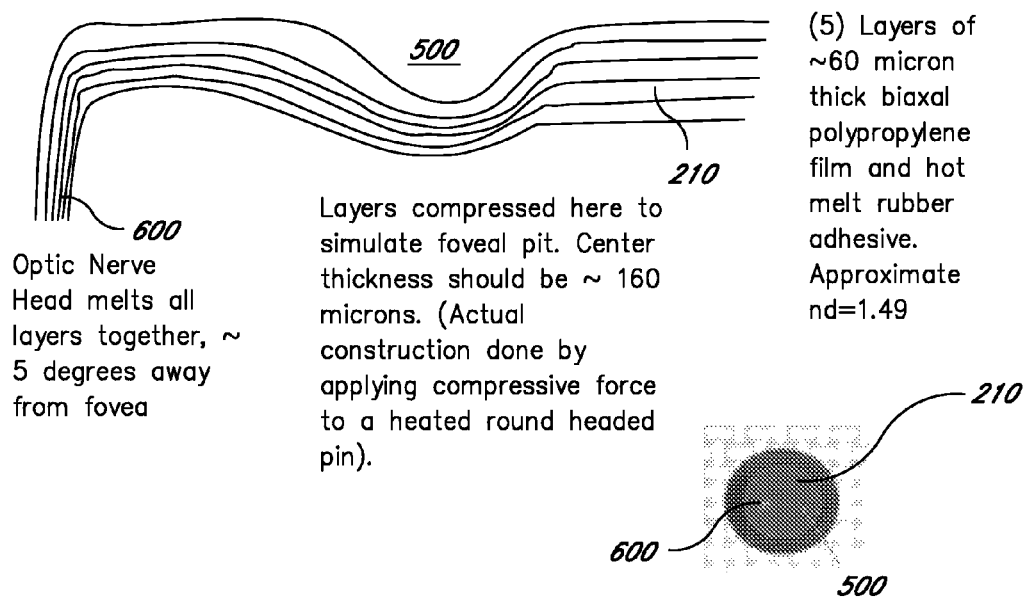
FIG. 9B Retina Construction on Water Bath Model
Cross Sectioal View

PHANTOM FOR RENDERING BIOLOGICAL TISSUE REGIONS

CLAIM OF PRIORITY

This application claims the benefit of U.S. Provisional Application No. 61/298,113 filed Jan. 25, 2010, entitled "MODEL EYE," and U.S. Provisional Application No. 61/425,124 filed Dec. 20, 2010, entitled "SOLID EYE MODEL FOR OPTHALMIC DIAGNOSTIC IMAGING." Each of the foregoing applications is incorporated by reference in its entirety.

BACKGROUND

1. Field of the Invention

The present disclosure relates generally to optical tissue analogs and phantoms, including but not limited to eye models for ophthalmic diagnostic imaging, as well as models for cardiovascular imaging, esophageal imaging, and dermatological imaging.

2. Description of the Related Art

Ophthalmic diagnostic instruments such as optical coherence (time domain, spectral domain, etc.) tomography (OCT) instruments, scanning laser ophthalmoscopes (SLO), and fundus cameras are useful for imaging. For example, OCTs are being used to make precise retinal thickness measurements to support the tracking of certain diseases, such as diabetic macular edema (DME) and glaucoma (base on nerve fiber layer thickness). Devices that can improve the quality of the measurements are desirable.

SUMMARY

One innovative aspect of the subject matter disclosed herein is an eye model. The eye model includes an assembly of one or more optically transmissive media. The one or more optically transmissive media has a first portion and a second portion. The one or more optically transmissive media provides similar optical properties as that between a corneal surface and a retina of an eye. A rendered retina can be disposed in the second portion of the assembly and be representative of the retina of an eye. The rendered retina can have one or more volume features associated with the retina of the eye.

In certain embodiments, the one or more optically transmissive media can be a single piece of optically transmissive material including the first portion and extending to the second portion. The first portion can define the rendered corneal surface and the second portion can define the rendered retina. The single piece of transmissive material can further define a pupil stop formed by a reduction in lateral dimension along an axis extending from the rendered corneal surface to the rendered retina. The eye model can further include a rendered choroidal/sclera reflector.

In the eye model according to certain embodiments, the one or more features can include one or more layers associated with the rendered retina. Each layer can have an index of refraction difference within each layer and/or scattering coefficient within each layer. The index of refraction and/or scattering coefficient can be adjusted (e.g., varied) so that the imaging instrument can resolve the separate layers. The one or more layers can further include a feature defining a rendered foveal pit or rendered optical nerve head. At least one layer (sometimes only one layer) can include nanoparticles. At least one other layer can also include a diffusion layer and this diffusion layer may be adjacent the nanoparticles in certain embodiments. In certain embodiments, at least one surface of the one or more layers has surface roughness. At least one interface between at least two layers can have surface roughness. In various embodiments, there is a difference in index of refraction between at least two layers. In some embodiments, the difference is less than about 0.1. In addition, at least two layers can be birefringent and have respective optic axes with different orientations.

In some embodiments, an eye model is provided. The eye model includes an assembly of one or more optically transmissive media. The one or more optically transmissive media can have a first portion and a second portion. The one or more optically transmissive media can provide similar optical properties as that between corneal surface and retina of an eye. A rendered retina can be formed on the second portion of the assembly and can be representative of the retina of an eye. The rendered retina can have one or more features formed by a computer controlled device from data representative of corresponding features associated with the retina of the eye. The computer controlled device can include a laser machining device. The data can be obtained by laser scanning of the corresponding features of the retina of the eye.

In certain embodiments, a method for fabricating a model eye is provided. The method can include obtaining data representative of one or more features associated with a retina of an eye; and rendering the one or more features on a substrate via a computer controlled laser device based on the data. The one or more features can include one or more topological layers associated with the retina. The one or more features can further include one or more local features on one or more of the layers. In some embodiments, the data can include first and second data files. The first file can have information about the one or more layers, and the second file can have information about the one or more local features.

Another innovative aspect is a phantom for mimicking biological tissue regions. The phantom includes an assembly of one or more optically transmissive media. The one or more optically transmissive media has a first portion and a second portion. The one or more optically transmissive media provides similar optical properties as that between a first tissue region and a second tissue region of an anatomical part. The first portion of the assembly has a first optical property and is representative of the first tissue region of the anatomical part. The second portion of the assembly has a second optical property and is representative of the second tissue region of the anatomical part. The second optical property of the second portion can be different than the first optical property of the first portion. The first portion can include a first layer and the second portion can include a second layer.

Certain embodiments may include non-ophthalmic anatomical parts (e.g., anatomical part other than eye and eye tissue). In certain embodiments of the phantom, the first optical property can include a first index of refraction, and the second optical property can include a second index of refraction. The difference between the first index of refraction and the second index of refraction can be less than about 0.1. The first optical property can also include a first optic axis oriented birefringence, and the second optical property can also include a second optic axis oriented birefringence. The difference between the first optic axis oriented birefringence and the second optic axis oriented birefringence can be approximately 90 degrees. In addition, the first optical property can include a first scattering coefficient, and the second optical property can include a second scattering coefficient. The first optical property can also include a first absorption coefficient, and the second optical property can also include a second absorption coefficient.

In a phantom in accordance with certain embodiments disclosed herein, at least one of the first portion or the second portion can include features associated with at least one of the first region or the second region respectively. The features can include an index of refraction difference within a layer and among different layers. The features can also include texturing. The texturing can include nanoparticles, pits, scratches, or other features.

As disclosed herein, the first tissue region can include at least a portion of a first tissue layer of a retina, and the second tissue region can include at least a portion of a second tissue layer of the retina. In other embodiments, the first tissue region can include at least a portion of a first tissue layer of a blood vessel, and the second tissue region can include at least a portion of a second tissue layer of the blood vessel. The blood vessels can be located at or near the heart. Certain embodiments of phantoms can include rendered regions of arterial tissue, e.g., including but not limited to those in the tunica intima, tunica media, and/or tunica adventitia. In yet other embodiments, the first tissue region can include at least a portion of a first tissue layer of an esophagus, and the second tissue region can include at least a portion of a second tissue layer of the esophagus. Embodiments of phantoms can include rendered regions of esophageal tissue, e.g., including but not limited to those in the mucosa (e.g., epithelium) and/or submucosa. The first tissue region of certain embodiments can include at least a portion of a first tissue layer of skin, and the second tissue region can include at least a portion of a second tissue layer of the skin. The rendered tissue layers of certain phantoms can include, for example, those in the epidermis, dermis, and/or subcutaneous tissue layers.

BRIEF DESCRIPTION OF THE DRAWINGS

FIG. 1E shows an isometric view of an example of an anatomic model, such as an eye model.

FIG. 1F shows a front view of the example anatomic model shown in FIG. 1E.

FIG. 1G shows a cross-sectional view of the example anatomic model shown in FIG. 1E.

FIG. 1H shows a close-up view of the circled region in FIG. 1G.

FIG. 4 schematically illustrates an example eye model with a layered retina.

FIGS. 9A-9D show examples of eye models including a foveal pit and an optic nerve head.

DETAILED DESCRIPTION

Figure 1A:
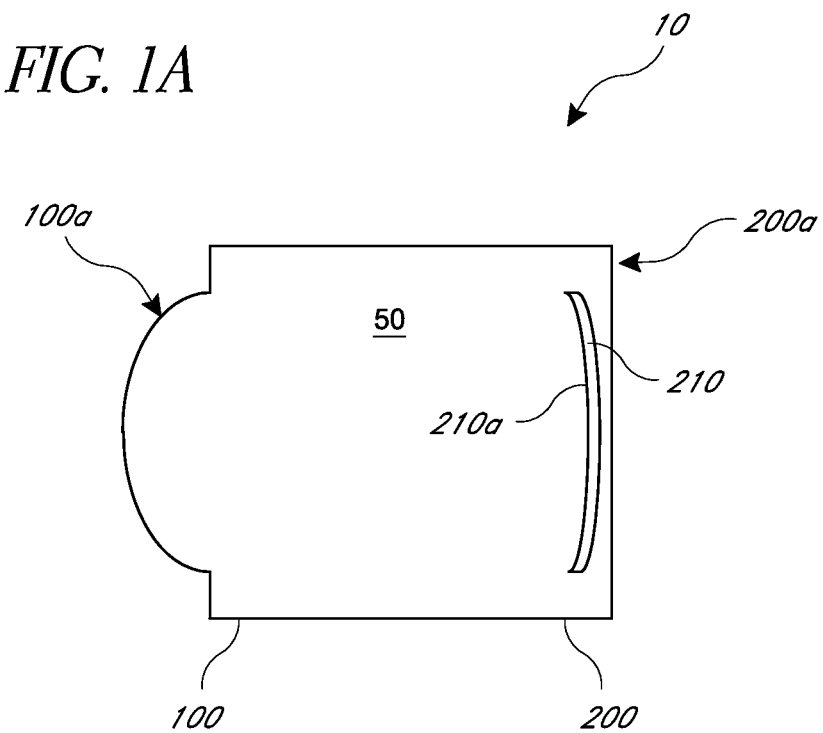
FIGS. 1A-1D schematically illustrate examples of anatomical models, such as eye models in accordance with certain embodiments described herein.

Embodiments disclosed herein include anatomical model structures, as well as methods of fabrication anatomical model structures. For example, the apparatus can be an eye model specifically designed for imaging by Optical Coherence Tomography (OCT), Scanning Laser Ophthalmoscope (SLO), and fundus camera instruments. Various embodiments of the apparatus can also be viewed by retinoscopes, slit-lamps, direct and indirect ophthalmoscopes, but in some embodiments, they can be optimized to be viewed by OCT, SLO, and fundus camera instruments. The apparatus can be useful for other instruments as well and need not be specifically designed for any particular one.

Certain embodiments of anatomical models as disclosed herein can address cross-calibration of machines by different manufacturers and technologies. For example, eye models can be used to address cases where time-domain OCT measures a different retinal thickness than spectral domain OCT, and even within the spectral domain OCT category where different instruments manufactured by different manufacturers measure the same clinical cohort of patients differently. Accordingly, reference and calibration devices and methodologies, such as a calibrated eye model, for these instruments may result in more accurate and consistent measurements. A good example includes diabetic macular edema trials, where retinal thickness is measured in clinics around the world by different machines of different manufacturers.

Anatomical models according to various embodiments described herein can also be used for improved training targets. Training to use diagnostic instruments done by imaging a willing subject has many drawbacks. Biological tissue, either ex vivo or in vitro, can be a poor training target. For example, once harvested, eye tissues can be constantly changing in terms of optical characteristics (e.g., corneas when harvested often become hazy and highly scattered) and once ex vivo, the optics are a function of hydration, a difficult quality to manage. Harvested biological tissue is expensive, relatively rare, requires special storage and handling conditions, and lasts a limited amount of time. Also, a limited number of animal tissues are an adequate analog for human tissues.

In vivo human tissue may also not be ideal for the stated need of a target. Human tissue can change, and the safety aspects of testing minimally invasive or non-invasive diagnostic instruments (e.g., ocular hazards of laser or SLD based OCT systems in repeated testing on humans, particularly in a factory environment) can be a factor. Even minimally invasive non-ocular diagnostic imaging can suffer for a good target, e.g., esophageal OCT. Also, tissue sample models can be useful for a trade show or demonstration, where dozens of these instruments may be demonstrated at the same time.

Benefits can thus be obtained for well-characterized optical tissue analogs or phantoms, such as disclosed herein, which can be configured as targets that are made of non-biological or minimally biological material that can be imaged on diagnostic instruments. In some embodiments, the target does not change significantly with time, requires no special handling, can be used as a calibration or transfer device, emulates optical characteristics of real tissue, can be engineered to show real disease or morphological states, allows for instrument training and demonstration, and/or is relatively inexpensive.

One or more examples of anatomical models disclosed herein can be designed to adequately demonstrate, test, or verify calibration of the performance of diagnostic instruments. In addition, one or more examples of a functioning anatomical model disclosed herein can simulate morphology/pathologies that can be imaged like real morphology/pathologies in the diseased anatomy. For example, some possible advantages that may be provided by certain embodiments of eye models include the ability to show non-"normal" retinas, e.g., retinas that are not normal morphology and may replicate certain pathologies. Again, this would aid students in the recognition of such retinas, and also serve to aid expert clinicians in the grading or classification of certain diseases, e.g., age-related macular degeneration. Some examples of morphology/pathology that would render well with this technology can include Diabetic Macular Edema (DME), Epiretinal Membrane (ERM), and Macular Hole.

Such anatomical models, which can be repeatedly made with the same morphology/pathology, can be used to train medical staff to spot such disease, and can also enable clinicians to agree on classification of disease, no matter what imaging instrument is looking at it. While an anatomical model may not completely replace a human subject in training, having such a model to practice on could assist easing the early part of the learning curve with these instruments. Other uses for models include uses in trade shows, demonstrations, and in product development or service by the manufacturer. Thus, certain embodiments of anatomical models described in this application can prove to be useful to a diverse group of clinicians, researchers, students, faculty, engineers, and technicians, etc. Other benefits are also possible. While various embodiments may provide one or more of these benefits, embodiments need not achieve any of these advantages in some cases.

Figure 1B:
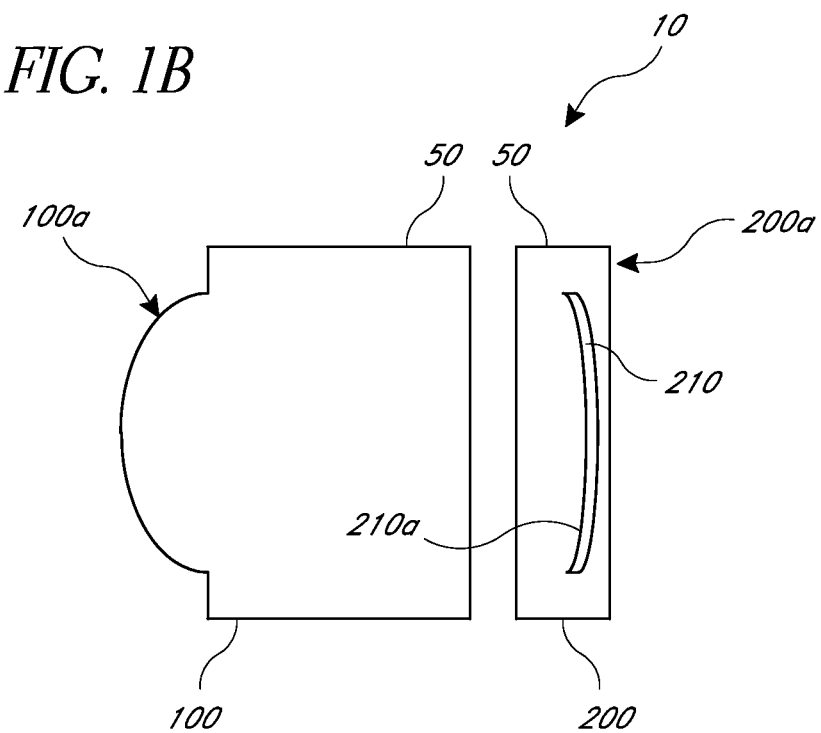

In accordance with certain embodiments disclosed herein, an anatomical eye model is provided. Features of certain embodiments of an eye model can include the retina and the optics. The retina is a light-sensitive tissue on the inner surface of the eye. In the front of the eye, the cornea admits light into the eye and refracts the light together with the lens, producing an image on the retina. FIGS. 1A-1D schematically illustrate examples of anatomical models, such as an eye model in accordance with certain embodiments described herein. The eye model 10 includes an assembly of one or more optically transmissive media 50. The one or more optically transmissive media can be formed from a single piece of optically transmissive material 50 as shown in FIG. 1A. The optically transmissive material 50 can be a glass or a polymer (e.g., plastic). Some examples include optical glass, poly (methyl methacrylate) (PMMA), polycarbonate, and polypropylene. Other materials can also be used. In other embodiments, the optically transmissive media 50 can be formed from more than one piece of optically transmissive material, either the same material or different, as shown in FIG. 1B.

The one or more optically transmissive media 50 is configured to provide similar optical properties to two different anatomical structures, such as for example, but not limited to, a corneal surface and retina of an eye. As seen in FIGS. 1A-1B, the optically transmissive media 50 has a first portion 100 and a second portion 200. The first portion 100 shows a curved surface 100a on an end opposite to the second portion 200. This curved surface 100a can be a refracting surface, e.g., representing the corneal surface. The curved surface 100a can have a typical radius of curvature of about 8 mm. In some embodiments, the radius of curvature can be in the range of about 6.5 mm to about 11.5 mm, e.g. about 6.5 mm to about 7.5 mm, about 7.5 to about 8.5 mm, about 8.5 mm to about 9.5 mm, about 9.5 mm to about 10.5 mm, or about 10.5 mm to about 11.5 mm. The curved surface 100a of the first portion 100 can be the primary refracting surface, but more than one surface can be used, e.g., a secondary refracting surface or a tertiary refracting surface. The curved surface 100a can be either spherical or aspherical. In some embodiments, this may be selected based on the resolution requirements of the eye model 10. An aspherized surface in certain embodiments can allow for better lateral and axial resolution.

Figure 1C:
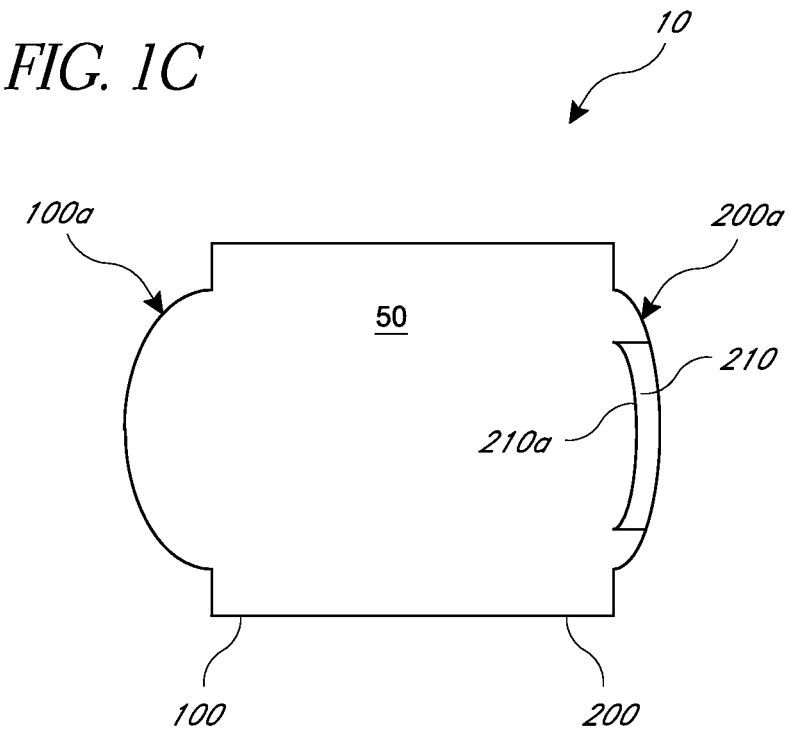
Figure 1D:
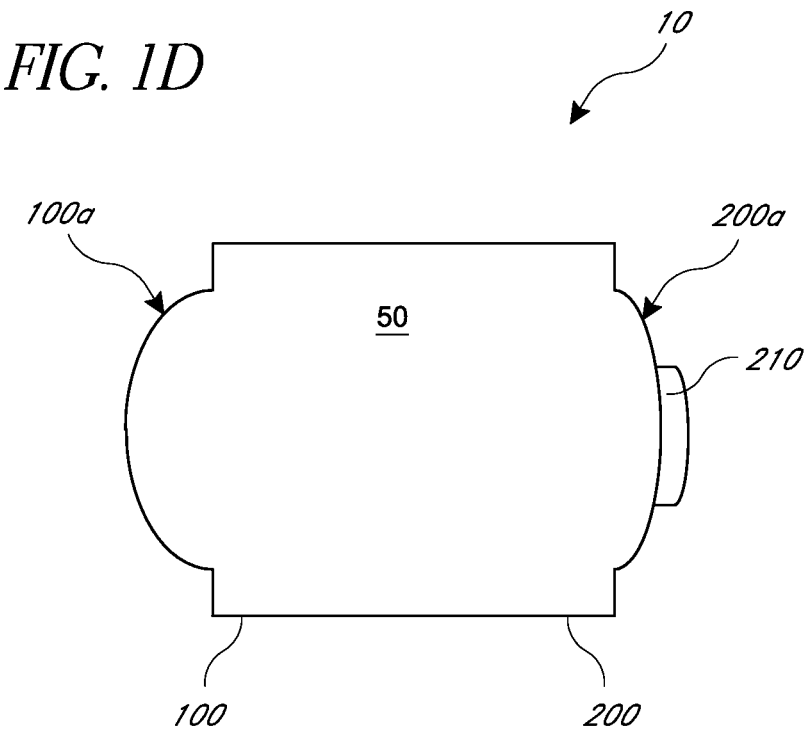

In FIGS. 1A-1B, the second portion 200 has a flat surface 200a on an end opposite to the first portion 100. However, in certain embodiments, the second portion 200 advantageously has a curved or partially curved surface 200a as shown in FIGS. 1C and 1D. A curved surface can be advantageous to allow for better instrument scanning. For example, a curved surface can allow for a wider field of view to remain in focus. In some embodiments, a hyperbolic surface is formed within the second portion 200 which can advantageously act as a curved substrate for a rendered retina 210. In other embodiments, a parabolic surface is formed. Still other shapes are possible.

In various embodiments, a rendered retina 210 is included in the second portion 200 of the assembly and representative of the retina of an eye. The rendered retina 210 has one or more features associated with the retina of the eye as will be discussed below. In certain embodiments, the rendered retina 210 can have a flat surface. However, as shown in FIG. 1A-1D, the rendered retina 210 can advantageously have a curved surface 210a on a side facing the first portion 100.

In certain embodiments, the optics of the first portion 100 are designed so as to allow for imaging the rendered retina 210, e.g., having a curved surface 210a, which can stay in focus (e.g., for about a 25-50 µm depth of focus) over the entire field of view (e.g., about +/−25 degrees) of the instrument. Such focus over the entire field of view can be achieved by the curved surface 210a of the rendered retina 210 substantially matching the surface of best focus, for example, of the scanned OCT beam. According to various embodiments, for example, even though different instruments can have different beam diameters and different depths of field, the instruments can be focusable such that the curved surface 210a is in focus. The surface curvature of the curved surface 210a can be substantially the same as the nominal radius of curvature of a human retina. For example, the radius of curvature can be about 12 mm. In certain embodiments, the radius of curvature of the rendered retina can be about 9.5 mm to about 14.5 mm, e.g., about 9.5 mm to about 10.5 mm, about 10.5 mm to about 11.5 mm, 11.5 mm to about 12.5 mm, about 12.5 to about 13.5 mm, or about 13.5 mm to about 14.5 mm.

In certain embodiments, the surface curvature of the curved surface 210a and/or curved surface 200a is aspherized to advantageously maintain focus. For example, FIG. 1E shows an isometric view of an example of an anatomical model, such as an eye model 10. FIG. 1F shows a front view of the example anatomic model shown in FIG. 1D. FIG. 1G shows a cross-sectional view of the example model shown in FIG. 1E. FIG. 1H is a blown up view of the circled region in FIG. 1G. An aspherized surface can be created in certain embodiments with various zones, including a central bump zone 201, an annular zone 202 surrounding the central bump zone, and a base cut zone 203.

The center of the central bump zone 201 can correspond to a center of a fovea or foveal pit. The fovea or foveal pit is a pit or depression within the retina that allows the light to hit the photoreceptor cells that give the sharpest image and most color perception. The curvature of the central bump zone 201 can be given by the equation $z(r)=0.122 \cos(3.14159r/2)^2 + ((-0.08333r^2)/[1+(1+0.02777r^2)^{0.5}]-0.3)$, which is applicable for radii from 0 mm to 1 mm. The curvature of the annular zone 202 surrounding the central bump zone 201 can be given by the equation $z(r)=(-0.08333r^2)/[1+(1+0.02777r^2)^{0.5}]-0.3$, which is applicable for radii from 1 mm to 2.4 mm. The curvature of the base cut zone 203 can be given by the equation $z(r)=(-0.08333r^2)/[1+(1+0.02777r^2)^{0.5}]$, which is applicable for radii from 2.73 mm to 6.64 mm. Accordingly, these surfaces are aspheric. Other shapes, possibly characterized by other equations, are possible.

Figure 2A:
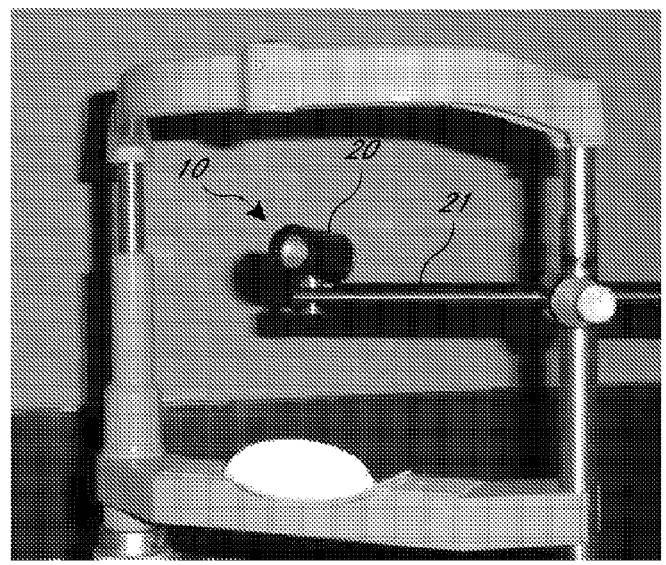
FIG. 2A shows an example eye model mounted on a chin rest compatible for use with various ophthalmic instruments for imaging.
Figure 2B:
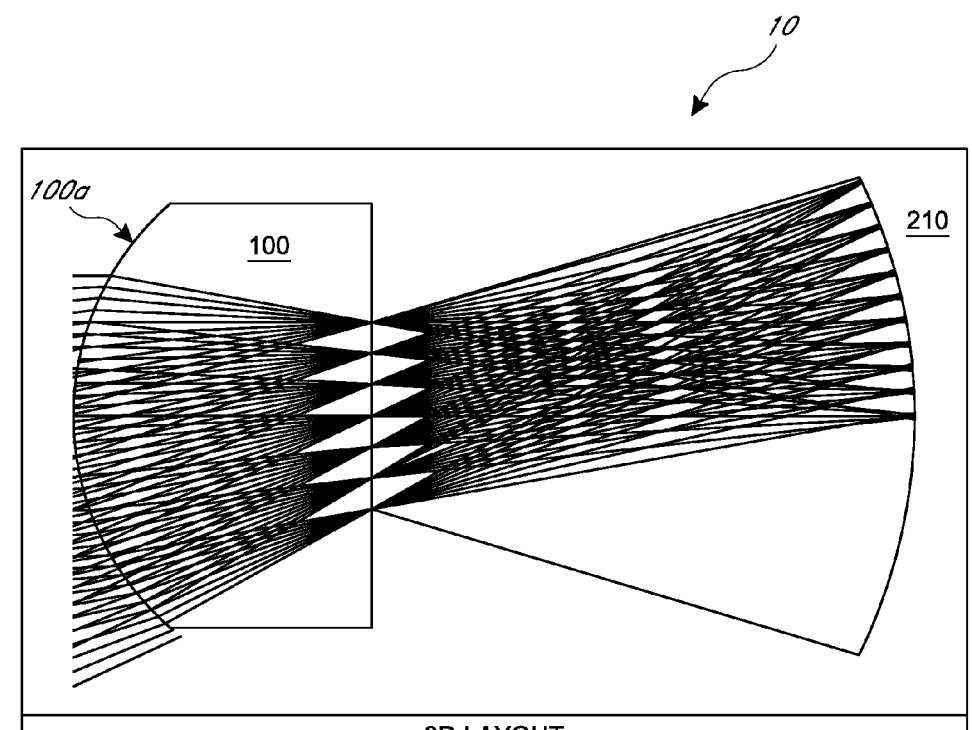
FIG. 2B shows an example ray trace for certain embodiments of an eye model.

FIG. 2A shows an example eye model 10 in accordance with certain embodiments described herein. The eye model 10 can include a housing 20, which advantageously allows the eye model 10 to be supported, for example, by a mount 21 on a chin rest compatible for use with various ophthalmic instruments for imaging. The model may thus be used with conventional OCT instruments, slit lamps, and other diagnostic equipment. FIG. 2B shows an example ray trace for certain embodiments of an eye model. This figure shows how a rendered retina 210 of certain embodiments of an eye model 10 can be imaged with a diagnostic instrument. The curved surface 100a of the first portion 100 defines a refracting surface, e.g., a corneal surface. The second portion 200 defines the rendered retina 210. As light shines on the curved surface 100a of first portion 100, the light refracts onto the rendered retina 210. The pupil plane is where the rays converge into a point. The pupil plane is the optical stop for the eye.

Figure 3A:
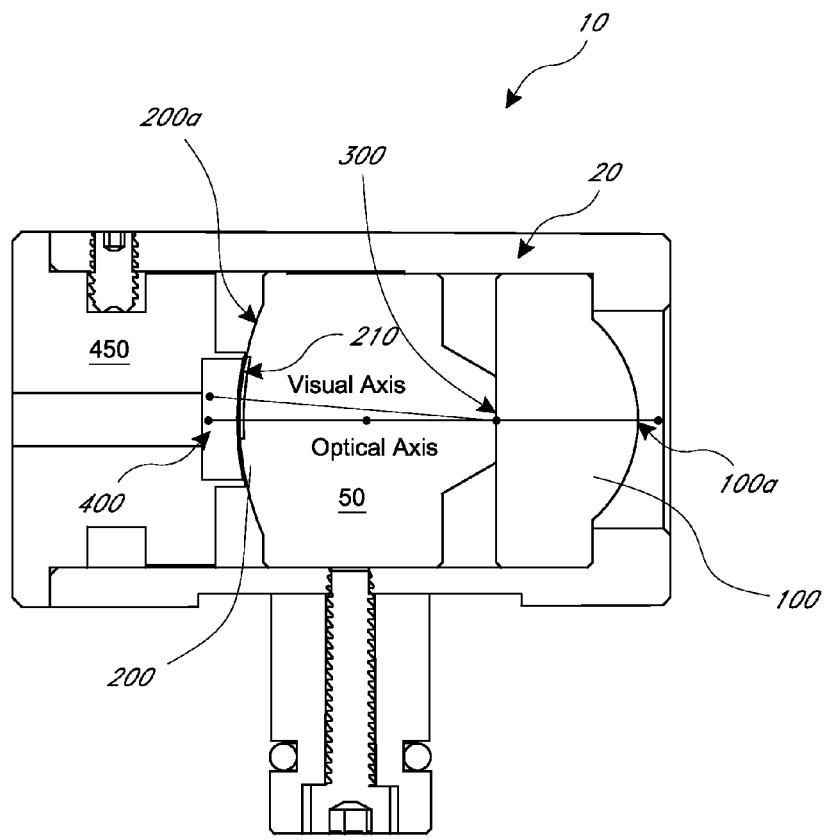
FIG. 3A is a cross-sectional view that schematically illustrates an example eye model in accordance with certain embodiments described herein.
Figure 3B:
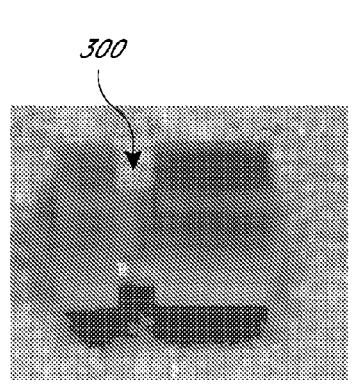
FIG. 3B shows an example eye model with a pupil stop.

FIG. 3A schematically illustrates an example eye model 10 in accordance with certain embodiments disclosed herein. As discussed above, the eye model 10 can include an assembly of one or more optically transmissive media 50. The one or more optically transmissive media 50 can include a first portion 100 and a second portion 200. The first portion 100 can define a curved or corneal surface 100a, e.g., having a radius of curvature of about 8 mm. This curvature, however, may be different. The first portion 100 of the eye model 10 can further include a pupil stop 300, which limits the amount of light reaching the retina. In certain embodiments, the rendered pupil stop 300 is the optical stop for the eye model 10. It can provide a target for initial alignment, as well as can limit scattered light and stray light from outside the instrument from being produced in the image. FIG. 3B shows an example eye model with a rendered pupil stop 300. In some embodiments, the rendered pupil stop 300 is located further back than that for a human pupil because an ocular lens is not included in the eye model 10. In these embodiments, the shape of the rendered corneal surface 100a can be designed to provide the refractive power associated with both a human cornea and lens by using a refractive index for the eye model 10 higher than that for a human eye, e.g., 1.49 v. 1.38.

In certain embodiments where the eye model 10 is formed from a single piece of optically transmissive media 50, e.g., a single piece of PMMA. The rendered pupil stop 300 can be formed by a reduction in lateral dimension along an axis extending from the corneal surface 100a to the rendered retina 210. See, for example, FIG. 3B. This reduced dimension can be formed in some embodiments by turning the assembly on a lathe. The effective diameter for this rendered pupil stop 300 can be, e.g., about 8 mm. This can represent a well dilated eye that is normal for ophthalmic imaging. In other embodiments, the effective diameter for the rendered pupil stop 300 can be modified as desired. In some embodiments, the effective diameter for the rendered pupil stop 300 can be in the range of about 6.5 mm to about 11.5 mm, e.g., about 6.5 mm to about 7.5 mm, about 7.5 to about 8.5 mm, about 8.5 mm to about 9.5 mm, about 9.5 mm to about 10.5 mm, or about 10.5 mm to about 11.5 mm.

As shown in FIG. 3A, the eye model 10 also includes a second portion 200. The second portion can define the rendered retina 210. The second portion 200 in this embodiment has a curved surface 200a that can act as a curved substrate for the rendered retina 210. The first portion and the second portion can be placed within a housing 20 which is in some embodiments can be configured to be attached to a chin rest compatible for use with various ophthalmic diagnostic imaging instruments.

In certain embodiments, the eye model 10 can further include a choroidal/sclera reflector 400. In the human eye, the sclera, the white wall of the eye protecting the internal features of the eyeball, is the tissue extending from the cornea to the back of the eye. The choroid lies between the retina and the sclera and absorbs scattered light to help control reflection.

In certain embodiments of the eye model 10, the choroidal/sclera 400 can be a silicone polymer. The silicone polymer can be in some embodiments, a red silicone adhesive 400a placed on a rear fitting 450. The rear fitting 450 can support the choroidal/sclera 400 and can be placed within housing 20. If a higher reflectivity is desired, e.g., more than that provided by about 80% absorption, a white silicone 400b can be substituted. The choroidal/sclera 400 can be any color and can be used to tune the absorptance of the eye model 10 and the return signal to the OCT. The rear fitting 450 can supply compressive force to the silicone choroidal/sclera 400, providing intimate contact with the rendered retinal 210 of the second portion 200, e.g., providing a secure seal and support, and can hold the whole assembly together. See, e.g., FIG. 3A.

Figure 3C:
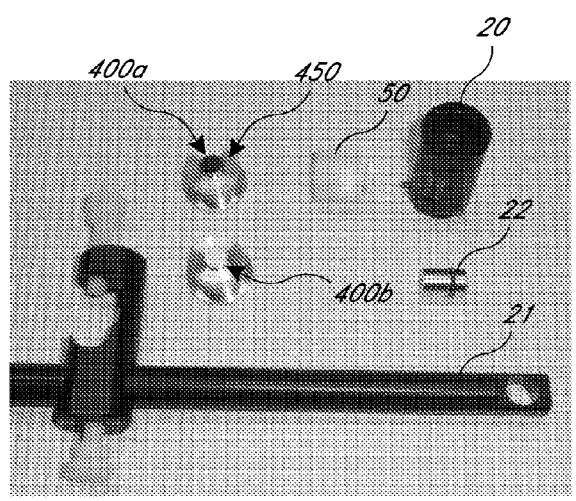
FIG. 3C shows example components of an eye model in accordance with certain embodiments described herein.

FIG. 3C shows components of an example eye model 10 in accordance with certain embodiments described herein. The example eye model 10 includes a housing 20, an optically transmissive media 50, and a choroidal/sclera reflector 400 having a red silicone 400a on a rear fitting 450. The example eye model 10 shown in FIG. 3C also includes a substitute choroidal/sclera reflector 400 having a white silicone 400b on a rear fitting 450. A mount 21 for mounting the eye on, for example, a diagnostic instrument, is also shown together with a connector 22 for connecting the model 10 to the mount 21.

Figure 5A:
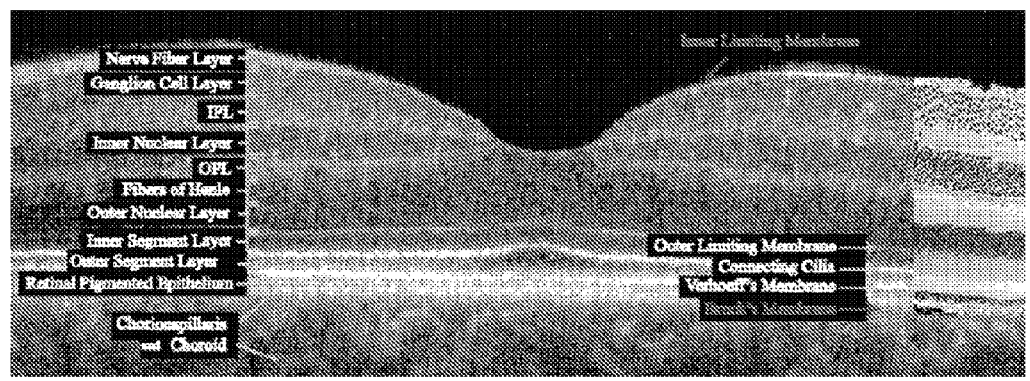
FIG. 5A is an OCT scan of tissue that illustrates the different layers that can be included in an eye model.

FIG. 4 schematically illustrates an example eye model with a layered retina. The rendered retina 210 can be constructed in layers, as is the human retina. Thus, as shown in FIG. 4, the retina can include one or more volume features comprising one or more layers 211 212. In some embodiments, the one or more features can be a plurality of layers. FIG. 5A shows an OCT scan of a human eye and illustrates the different layers that can be included in an eye model 10. The rendered retina 210 can include, for example, one or more of various layers including but not limited to seven layers: (1) nerve fiber layer, (2) ganglion cell and inner plexiform layer (IPL), (3) inner nuclear layer, (4) outer nuclear, fibers of Henle, outer plexiform layer (OPL), (5) inner and outer segment layer, (6) retinal pigment epithelium (RPE) layer, and (7) choroidal transition layer. The nerve fiber layer will typically be on the top, and the choroidal transition layer on the bottom. Various modifications can be made in combining and separating the layers. For example, the nerve fiber layer and the ganglion cell and inner plexiform layer can be parts of the same physical layer, but with the scattering top surface of the layer can appear as the nerve fiber layer. Some embodiments do not include all the layers described above, and other embodiments incorporate additional layers. For example, a choroidal space can also be fabricated as a layer of the retina.

Figure 5B:
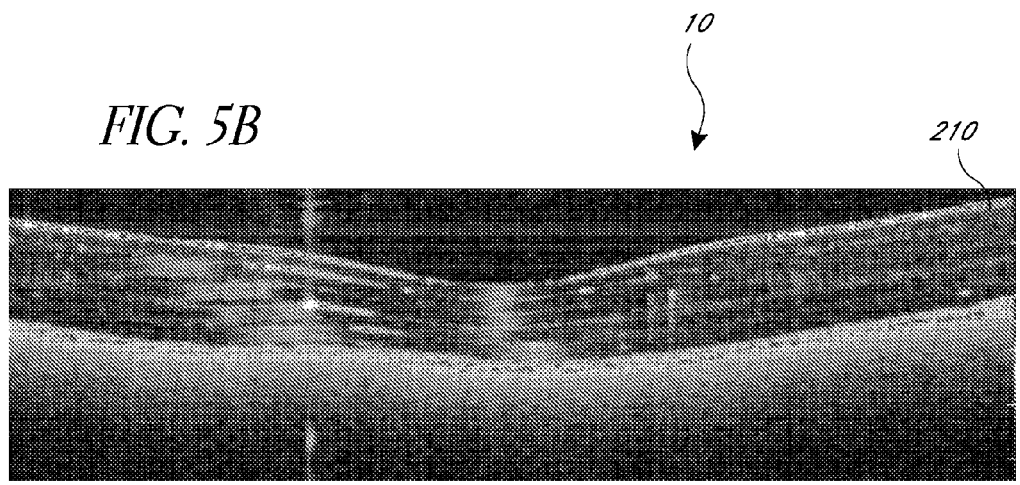
FIG. 5B shows an image of an example eye model with multiple layers as viewed with an OCT instrument.

FIG. 5B shows an image of an example eye model 10 as viewed with an OCT instrument. As can be seen, the distinct boundary layers in the rendered retina 210 can be viewed. In certain embodiments, the distinct individual boundaries can be seen by modifying scattering characteristics of the surface of the layers, as will be disclosed further below.

The thickness of each layer can be in a range of about 10 microns to about 100 microns (e.g., about 50 microns), which is similar to the dimensions in a human retina. Thus, the thickness of a layer can be in the range of about 5 microns to about 15 microns, about 15 microns to about 25 microns, about 25 microns to about 35 microns, about 35 microns to about 45 microns, about 45 microns to about 55 microns, about 55 microns to about 65 microns, about 65 microns to about 75 microns, about 75 microns to about 85 microns, about 85 microns to about 95 microns, or about 95 microns to about 105 microns. In some embodiments, the combined layers of the rendered retina 210 can be about 300 microns in thickness and about 4.8 mm across, which is sufficient for most OCT imagers. In other embodiments, the dimensions can be larger, while in other embodiments, smaller. For example, in certain embodiments, the thickness of the rendered retina 210 can be in the range of about 150 microns to about 250 microns, about 250 microns to about 350 microns, about 350 microns to about 450 microns, or about 450 microns to about 550 microns. In certain embodiments, the length of the rendered retina 210 can be in the range of about 3.5 mm to about 4.5 mm, about 4.5 mm to about 5.5 mm, or about 5.5 mm to about 6.5 mm, or even larger. As new diagnostic instruments develop, these dimensions can be modified accordingly.

There are many embodiments as to how the layers can be constructed. An example embodiment can include laser scanning the rendered retina 210. For example, a laser scanned rendered retina 210 can be created from data sets from an OCT itself or from another type of instrument. The data can correspond to features in the eye which can then be formed directly into a glass or polymer substrate layer by layer. For example, a laser directed by the data set can scan the glass or polymer substrate to form features therein. The features in the substrate will accordingly correspond to the features specified by the data set. This process can be used to create a three-dimensional rendered retina 210, which is substantially anatomically correct to the extent the data will allow. The optical properties of each layer of the imaged rendered retina 210 can imitate the corresponding layers in a real human retina. For example, as described below, each layer can have an index of refraction difference within each layer and scattering coefficient within each layer. Laser scanning is not limited to forming features in glass or polymer as other materials may possibly be used.

Figure 6A:
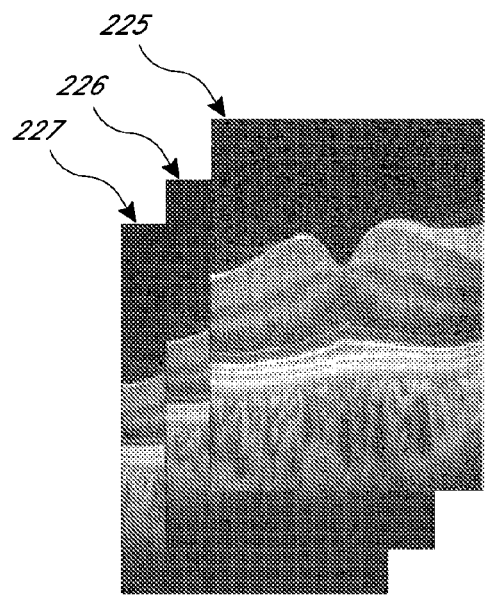
FIGS. 6A-6D show an example image of a real eye and a laser scanning process in accordance with certain embodiments described herein.
Figure 6B:
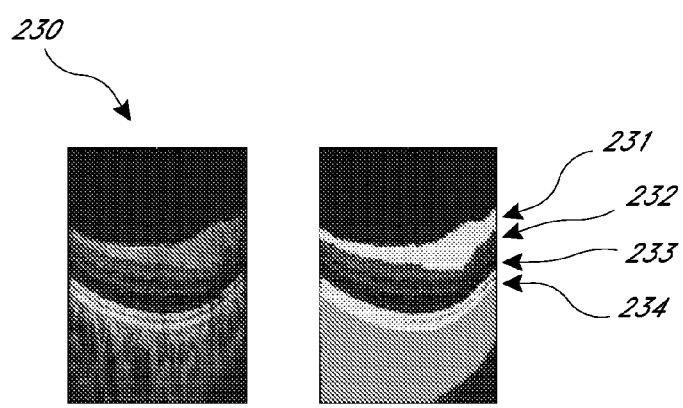

In accordance with certain embodiments, FIGS. 6A-6D show an example image of a real eye and a laser scanning process. As shown in FIG. 6A, the raw OCT (or CT or MRI or SLO or other data from another imaging instrument) data comes in "slices" or frames 225 226 227 otherwise referred to as B-scans. Referring to FIG. 6B, the frames are compiled into a 3D voxel data set 230, from which layers are identified, selected and converted into separate 3D files, e.g., .IGES or .sldprt, 231 232 233 234. These layers correspond to the anatomical layers of the retina, and can be "re-warped" to correspond to real retinal curvature, as well as maintaining the unique topology of each layer. See FIG. 6C. Each layer file, at the laser, can be assigned a scan speed and power level. This can correspond to the refractive index difference ($\Delta n$) and/or scattering coefficient characteristic of that layer in the model retina that the real layer would possess. In addition, the layer files can include information on the refractive index difference compared to other layers, e.g. compared to adjacent layers. For example, a retinal pigment epithelium (RPE) layer has the largest $\Delta n$ as compared to the adjacent layers and also has the largest scattering coefficient in the retina.

In various embodiments, a laser scanning system can re-create an optical retina within a substrate, e.g., PMMA material, by precise, localized (e.g., spot dia. <4 µm) changes in index of refraction. The index of refraction changes occur by local heating and polymeric cross-linking changes to the polymer, controlled by scan rate, laser power, and/or spot size. Very high power or low scan rates can result in thermal buildup exceeding thermal diffusion, to thereby cause micro vacuoles to be created, thus effectively creating a high local refractive index difference ($\Delta n$) at that point (pixel or voxel), which has an overall effect of increasing the effective scattering coefficient of the scanned media. Smaller $\Delta n$'s can be created by lower power or higher scan rates, and can approximate the $\Delta n$'s present within the retinal layers.

Figure 6C:
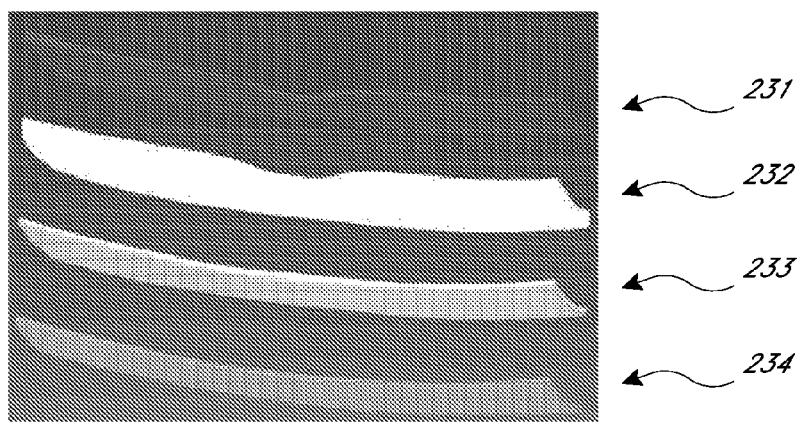
Figure 6D:
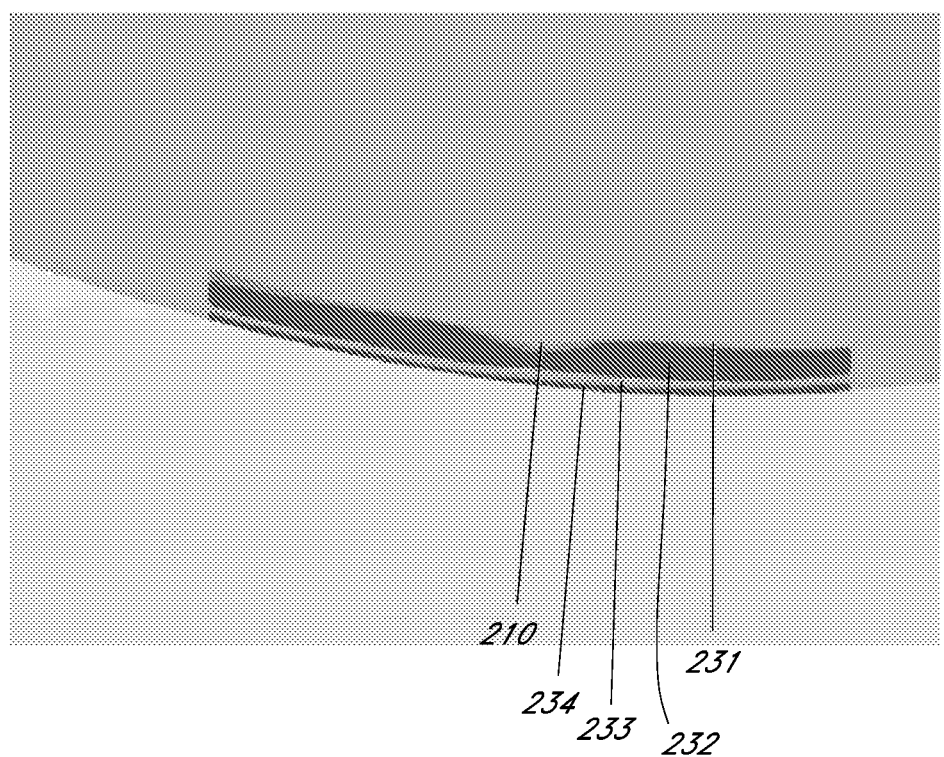

FIG. 6D shows an example of the individual layers being raster scanned into the solid eye model substrate 200 by a laser, until the eye model retina 210 is "built." This approach can be used to form, for example, the four layers 231 232 233 234 shown in FIGS. 6C and 6D. More or less layers may be included formed in other embodiments. In some embodiments, it makes sense to scan in layers down to the choroid/sclera 400, and then add bulk scattering reflection materials, such as silicone or Spectralon®, to simulate the choroid and sclera. Other layer can also be formed by laser scanning.

Figure 7:
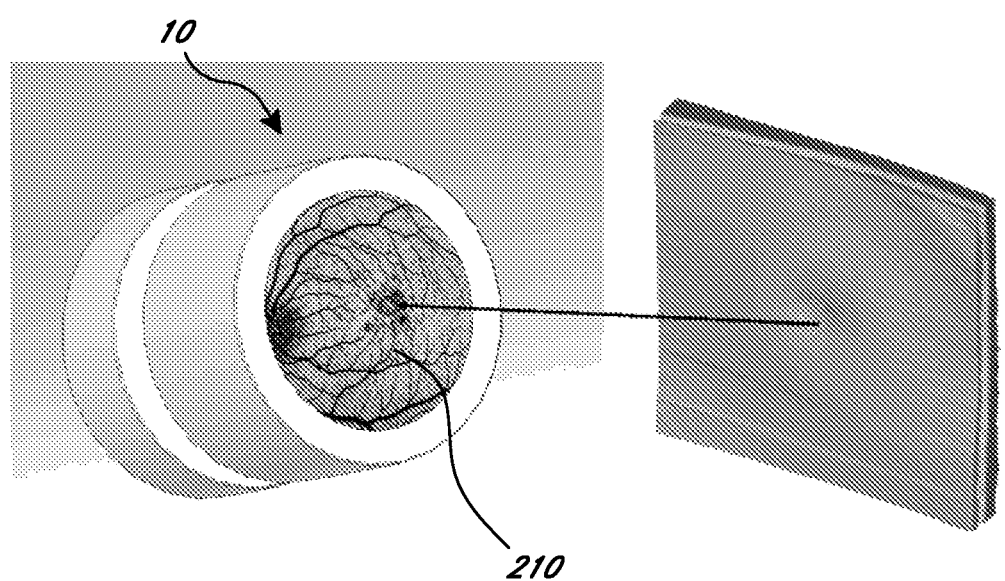
FIG. 7 shows an example embodiment of an eye model including details of vasculature features on or within one or more of the topology layers.

FIG. 7 shows an example embodiment of an eye model including details of vasculature features on or within one or more of the topology layers. Typical OCT images can be devoid of much vasculature, in that most OCT scans are done in and around the avascular fovea. As shown in FIG. 7, arteries, veins and capillary data can be added from SLO or fundus camera files similarly turned into laser scan data. These files can facilitate rendering of details such as vasculature features on or within one or more of the topology layers. These files can be separate from the topology layer files.

As described above, an eye model 10 can include an assembly of one or more optically transmissive media 50 having a first portion 100 and a second portion 200. The one or more optically transmissive media 50 can be configured to provide similar optical properties as that between corneal surface and retina of an eye. A rendered retina 210 can be formed on the second portion 200 of the assembly and can be representative of the retina of an eye. The rendered retina 210 can have one or more features formed by a computer controlled device from data representative of corresponding features associated with the retina of the eye.

According to certain embodiments described herein, the computer controlled device includes a laser machining device. The data can be obtained by laser scanning of the corresponding features of the retina of the eye.

Figure 8:
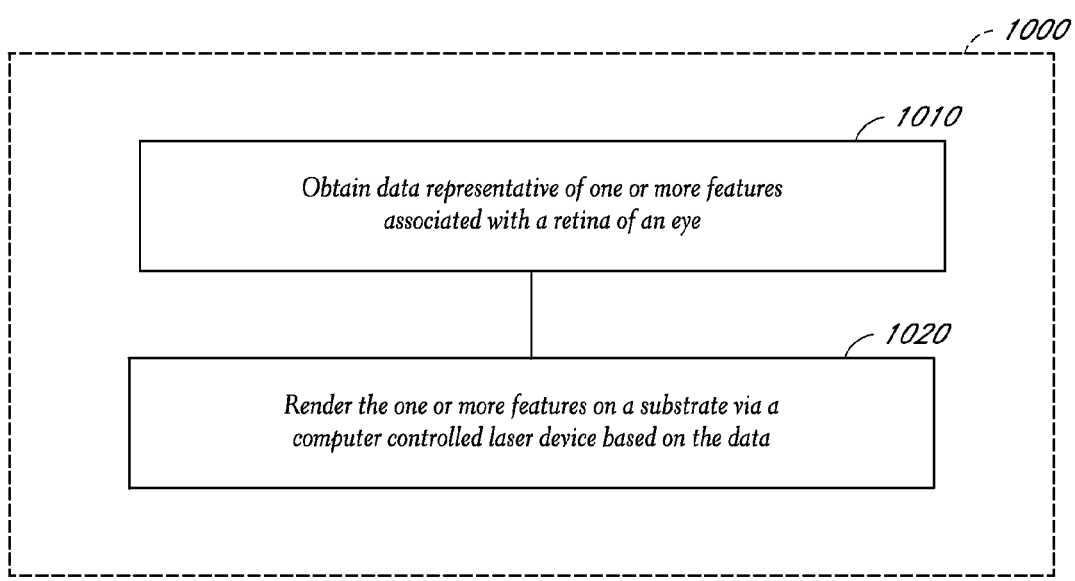
FIG. 8 shows an example method for fabricating an eye model in accordance with certain embodiments described herein.

Thus, in certain embodiments as shown in FIG. 8, a method 1000 for fabricating an eye model is provided. The method 1000 includes obtaining data representative of one or more features associated with a retina of an eye as shown in block 1010. The method 1000 also includes rendering the one or more features on one or more substrate via a computer controlled laser device based on the data as shown in block 1020. The one or more features can include one or more topological layers associated with the retina. The one or more features can further include one or more local features on one or more of the layers. In some embodiments, the data includes first and second data files. The first file can have information about the one or more layers, while the second file can have information about the one or more local features. In some embodiments, for example, the first file can include information on the index of refraction difference or scattering coefficient for the one or more layers. In addition, the second file can include information about vascular features.

In addition to the laser scanning method previously described, there are many other possible ways to create an eye model 10 with a layered rendered retina 210. In fabricating the model eye, the various layers can be adhered, molded on, applied, deposited, sprayed or in any other way attached together and/or to the substrate of the second portion 200 or other substrate or surface. Other methods of fabricating the retina may be used. In some embodiments, a retinal zone could be engraved away, and refilled with an assortment of refractive medium thereby forming multiple layers.

In certain situations, the laser scanning method can better model and simulate fine structural and refractive details found in the retina. For example, the foveal pit and optic nerve head are example structures that can be scanned and rendered well using the laser scanning method.

Thus, in certain embodiments, the one or more layers can further include a feature defining a foveal pit and/or optic nerve head. FIGS. 9A-9D show examples of eye models including a foveal pit and an optic nerve head. These figures will be discussed below. In the human retina are photoreceptor cells that convert light into signals. The signals are carried by the optic nerve to the brain. The fovea or foveal pit is a pit or depression within the retina that allows the light to hit the photoreceptor cells that give the sharpest image and most color perception.

A schematic of an example eye model 10 is shown in FIG. 9A. The example eye model 10 can include an assembly of one or more optically transmissive media 50 having a first portion 100 and a second portion 200. The optically transmissive media 50 having a first portion 100 and a second portion 200 can include a single piece of optically transmissive material including the first portion 100 and extending to the second portion 200. The one or more optically transmissive media 50 can include a glass, a polymer, or a combination thereof. In certain embodiments, the eye model 10 is a substantially solid state assembly. In some embodiments, the one or more optically transmissive media 50 can include a liquid, e.g., water, liquid polymers, and oils. In certain embodiments, however, substantially no liquid is included between the rendered corneal surface 100a and rendered retina 210, e.g., a substantially non-liquid assembly. Advantages of an assembly without liquid include a reduced risk for contamination. In a water bath, for example, there is the possibility for mold, algae, and fungi. The one or more optically transmissive media 50 can be configured to provide similar optical properties as that between a corneal surface and retina of an eye. The first portion 100 shows a curved surface 100a and can be a refracting surface, e.g., representing the corneal surface. The curved surface 100a can be made of a glass or polymer as described above.

In various embodiments, a rendered retina 210 can be disposed on the second portion 200 and be representative of the retina of an eye. The rendered retina can include a layer or a plurality of layers. In one embodiment, as shown in FIG. 9A, the rendered retina 210 includes at least five layers. Such a rendered retina 210 can be used regardless of whether a liquid or non-liquid medium is used between the rendered corneal surface 100a and the rendered retina 210. A cross sectional view of the five layers is shown in FIG. 9B. In this example, the eye model 10 can be created by adhering five layers of about 60 micron thick biaxial polypropylene film and hot melt rubber adhesive. The index of refraction was approximately 1.49.

In certain embodiments, a layer can be a transparent layer having a natural birefringence and polarization property. The rendered retina 210 can include a stack of transparent layers, with each layer having a natural birefringence and polarization property. An example of a transparent layer having birefringence is polypropylene tape having a thickness in a range of about 10 microns to about 100 microns (e.g., about 50 microns). Each layer can be adhered to another layer by an adhesive. Thus, materials for the layers can include polypropylene film and hot melt rubber adhesive. Polycarbonate, which has a natural birefringence, can also be used. Additionally, birefringence can be induced in many materials by deforming it, and thus many various materials can be used. In some embodiments, the combined layer (e.g., seven) of the rendered retina 210 can be about 300 microns in thickness and about 4.8 mm across. In certain embodiments, the dimensions can be larger, while in other embodiments, smaller.

In certain embodiments, the polarization properties of at least two adjacent layers can be different. For example, a first layer can have a first optic axis oriented birefringence and a second layer can have a second optic axis oriented birefringence different than the first. In some embodiments, each layer can have its own optic axis oriented birefringence that is different than the optic axis oriented birefringence of a neighboring layer, e.g., no two adjacent layers are oriented in the same direction. For example, each layer can be oriented such that its optic axis oriented birefringence is approximately 90 degrees from the neighboring layer. As another example, the optic axis oriented birefringence can be oriented such that its optic axis oriented birefringence is approximately 45 degrees from the adjacent layer. Other angles are possible. For example, any orientation that can provide a layer birefringence difference similar to the difference in natural tissue layer can be used. In various embodiments, at least two layers have differently oriented optic axes or birefringence properties, although each adjacent layer need not be different. By having different oriented optic axes or birefringence properties, polarization sensitive OCTs can detect the layers better.

Figure 9C:
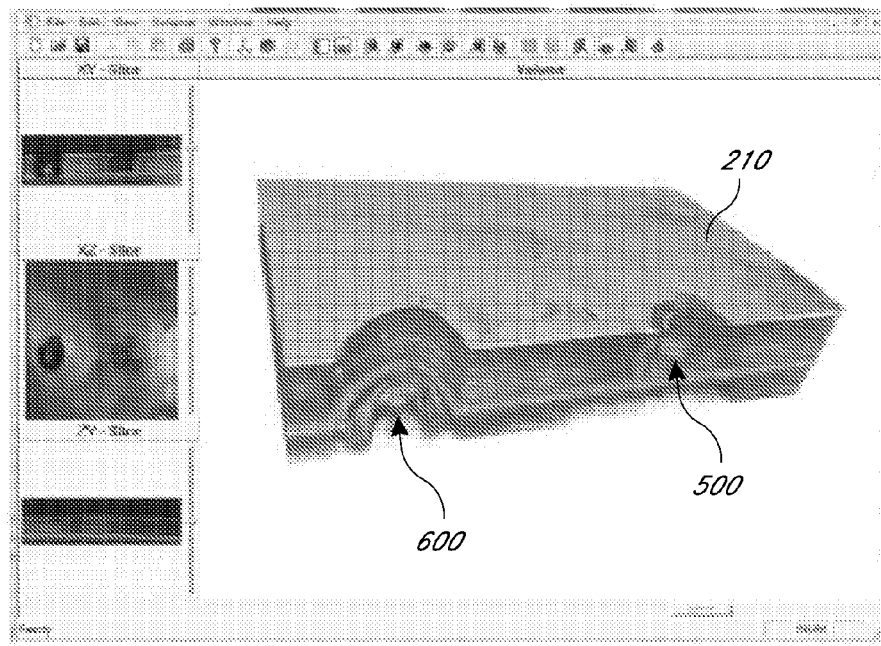

As shown in FIG. 9B, the layers of the rendered retina 210 of the example eye model 10 were compressed to simulate a foveal pit 500. The actual construction of the rendered foveal pit 500, e.g., as shown in the lower right corner of FIG. 9B, was performed by applying compressive force to a heated round headed pin. Other methods are possible. Photographic images of the layers of the eye model 10 can be found in FIGS. 9C-9D, including the rendered foveal pit 500.

Figure 10A:
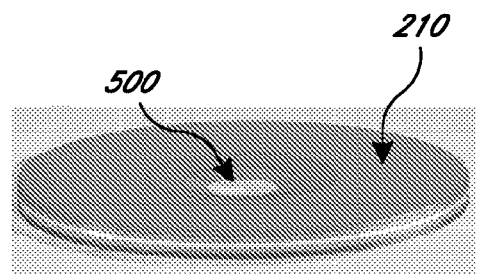
FIGS. 10A-10C show an example of a simulated foveal pit.
Figure 10B:
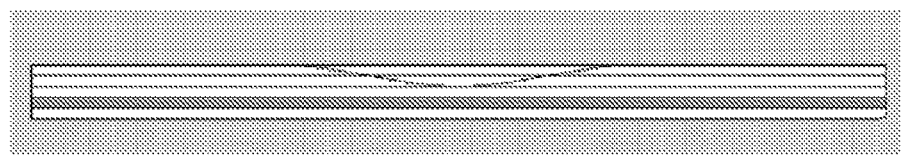
Figure 10C:
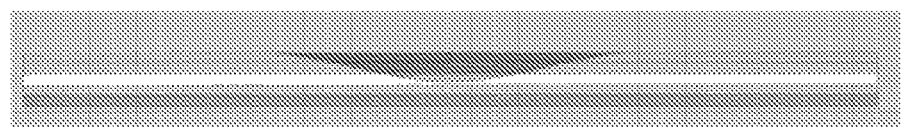

FIGS. 10A-10C show another example of a simulated foveal pit 500. The rendered foveal pit 500 can be defined on the stacked retina subassembly, e.g., the rendered retina 210, so as to have a dimension similar to that of a typical human foveal pit (e.g., about 120 microns). In some embodiments, the depth of the rendered foveal pit 500 can be in the range of about 95 microns to about 175 microns, e.g., 95 microns to about 105 microns, about 105 microns to about 115 microns, about 115 microns to about 125 microns, about 125 microns to about 135 microns, about 135 microns to about 145 microns, about 145 microns to about 155 microns, about 155 microns to about 165 microns, or about 165 microns to about 175 microns. In the example shown in FIGS. 10A-10C, the center thickness was about 160 microns deep. The rendered foveal pit 500 can include an ablated (or removed) portion of the rendered retina 210 as well as a compressed portion in various embodiments. Certain embodiments of the first portion 100 can include a substantially similar mirror of the rendered foveal pit 500, such that when the rendered retina 210 with the rendered foveal pit 500 is mated to the eye model optic surface of the first portion 100, there is a substantial fit with little or no airspace.

Figure 9D:
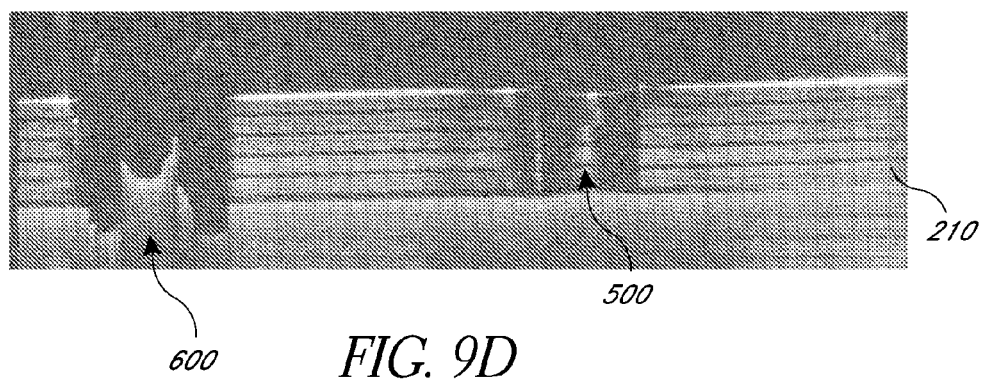

Certain embodiments of the eye model 10 can also include a rendered optic nerve head 600 as shown in the FIGS. 9D and 9E. The rendered optic nerve head 600 can melt all the layers together as shown in FIG. 9B. This typically occurs about 15 degrees away from the fovea pit 500. In certain embodiments, the rendered optic nerve head 600 can be included in a layer or plurality of layers of the rendered retina 210. For example, the rendered optic nerve head 600 can be formed by fusing a group of fibrils, e.g., plastic fibrils with a diameter between about 5-50 microns, together in a sheath. As the fibrils are fused together, the tops of the fibrils can be positioned onto a layer that can conform to the retinal curvature. The center of the sheath can then be cupped with a depression, e.g., by a heat molding tool. In some embodiments, the rendered optic nerve head 600 can occur about 5 degrees to about 20 degrees away from the foveal pit 500, e.g., about 3 degrees to about 5 degrees, about 4 degrees to about 6 degrees, about 5 degrees to about 7 degrees, about 6 degrees to about 8 degrees, about 7 degrees to about 9 degrees, about 8 degrees to about 10 degrees, about 9 degrees to about 11 degrees, about 10 degrees to about 12 degrees, about 11 degrees to about 13 degrees, about 12 degrees to about 14 degrees, about 13 degrees to about 15 degrees, about 14 degrees to about 16 degrees, about 15 degrees to about 17 degrees, about 16 degrees to about 18 degrees, about 17 degrees to about 19 degrees, or about 18 degrees to about 20 degrees away from the rendered foveal pit 500.

Figure 11:
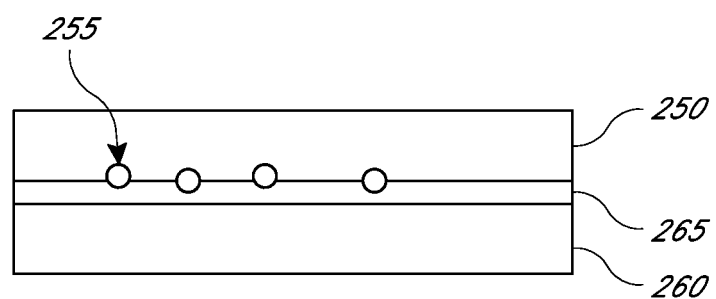
FIG. 11 shows a cross-sectional view of layers of an example eye model in accordance with certain embodiments described herein showing a layer including nanoparticles.

Certain embodiments of the eye model 10 can include additional features within the layer or within a plurality of layers. FIG. 11 shows a cross sectional view of layers of an example eye model in accordance with certain embodiments described herein showing a layer including nanoparticles. As shown in FIG. 11, at least one layer of the eye model 10 represents the retinal pigment epithelium layer (RPE) 250. The RPE layer helps enhance vision by absorbing light to prevent scattering. The RPE layer has melanin crystals (dark pigment), thus the layer 250 of the eye model 10 can include nanoparticles 255 to mimic the natural melanin crystals and thus to mimic the scattering mechanism in the RPE layer. SLOs, e.g., Heidelberg Retina Tomograph (HRT), can be used to look at these layers. In one embodiment, a thin layer of black carbon nanoparticles is included on the adhesive side of a transparent tape. The amount of nanoparticles 255 can be selected so as to maintain adhesive properties of the tape. The average size of the nanoparticles 255 can be in a range of about 10 nm to about 300 nm. An example of black carbon nanoparticles that can be used is 30 nm average-size NP-C available from MTI Corporation (Richmond, Calif.).

A second layer 260 of the eye model 10 can represent the choroidal transition layer. This rendered choroidal transition layer 260 can include a diffusion layer 265, which can advantageously allow certain embodiments to mimic the transition between two different scattering coefficients. For example, the top of the choroid has more capillaries than the deeper choroid resulting in different scattering coefficients. In certain embodiments, the adhesive side of the rendered RPE layer 220 can be adhered to the diffusion layer 265 such that the layer of nanoparticles 255 is sandwiched between the tape of the rendered RPE layer 250 and the diffusion layer 265. In other embodiments, the nanoparticles can be included in a single layer to help mimic the scattering mechanism, e.g, in a single rendered RPE layer or another rendered tissue layer or layers.

In addition, one or more surfaces of a layer can include features such as a high density of pits and scratches having dimensions approximately in or near a range of wavelength of light, e.g., about 0.7 to about 300 microns. In certain embodiments, each of the layers (e.g., 5 or 7, etc.) in the rendered retina may be roughened. One layer, two or more, three or more, four or more, five or more, six or more, or seven or more layers may be roughened. Thus, in certain embodiments, at least one layer has surface roughness. In various embodiments, the interfaces between layers have roughness. This can create a scattering interface visible to the OCT which operates in the near infrared wavelengths.

In addition to the features within each layer, certain embodiments feature differences between two layers. As mentioned above, the polarization orientation between two layers can be different. As another example, the difference in index of refraction between two adjacent layers in an actual retina can be mimicked in certain embodiments of the eye model 10. For example, one or more layers can comprise at least a first layer 211 and a second layer 212. See, e.g., FIG. 4. The first layer 211 can have a first index of refraction and the second layer 212 can have a second index of refraction. In certain situations, a difference in index of refraction is what optical coherence tomographers report as brightness, or gain, in their images. This condition is predominant in tissues where there is low scattering, e.g., ophthalmic tissue including retina. As an example, a vitreous interface has an index of refraction of 1.38 and the RPE layer has an index of refraction of 1.42. The RPE layer also has a much higher total scattering coefficient $\mu_s$, and thus appears brighter. See FIGS. 5A-5B. An important characteristic in creating optical tissue phantoms is the difference in index of refraction between two layers, not the absolute index of refraction per se. There are many more materials that can be used to create layers with absolute indices in and around 1.5, than there are with indices in and around 1.38, the natural absolute nominal index of refraction of retinal tissue.

To mimic this characteristic in the eye model 10 in certain embodiments, instead of using materials with the same absolute indices of refraction, e.g., first material having an index of refraction of 1.38 for the first layer 211 and a second material having an index of refraction 1.42 for the second layer 212, certain embodiments can match to a reasonable degree the index of refraction difference between the two adjacent tissues, e.g., 0.04. In some embodiments, the index of refraction difference can be less than about 0.1, less than about 0.09, less than about 0.08, less than about 0.07, less than about 0.06, less than about 0.05, less than about 0.04, less than about 0.03, less than about 0.02, and about 0.01.

Certain embodiments described herein are examples of models that apply to ophthalmology. While such examples are described in the context of diagnostic applications, it will be understood that one or more features of the present disclosure can be utilized in diagnostic and/or therapeutic applications, e.g., in ophthalmology. Examples of therapeutic applications can include testing or calibration of therapeutic instruments. In other embodiments, the tissue analogs or phantoms can apply to fields beyond ophthalmology. For example, as discussed above, the optical properties of tissue can be substantially mimicked by man-made materials. While not many man-made materials have exactly the same absolute indices of refraction as tissues (n=1.34 to 1.42), certain embodiments can match to a reasonable degree the index of refraction difference (Δn) between adjacent tissues.

Figure 12:
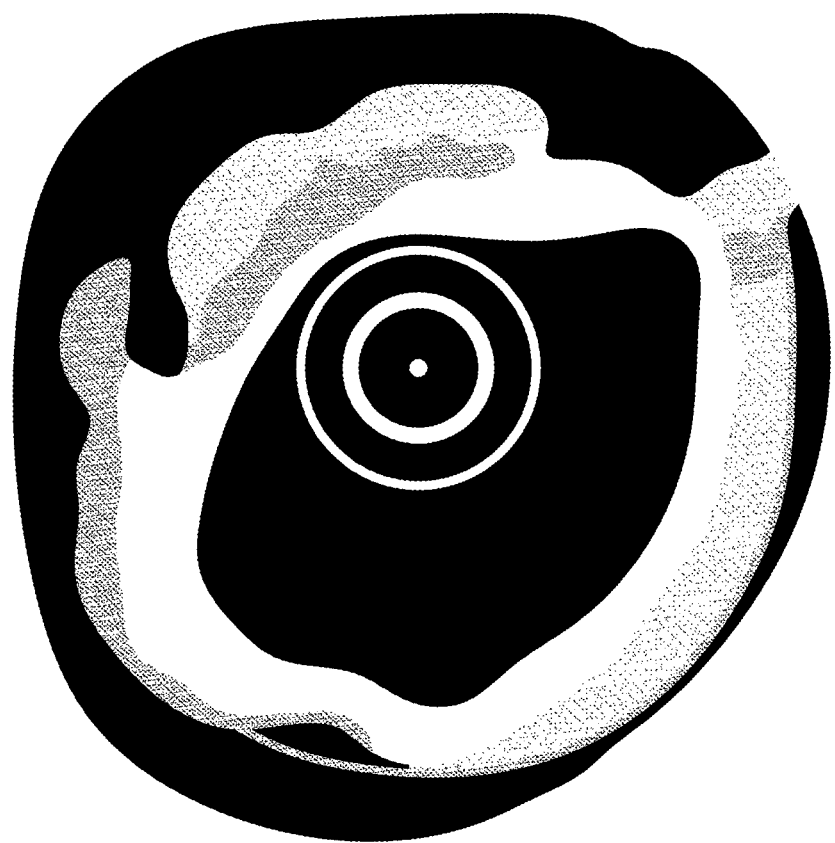
FIGS. 12-14 show example schematics of scattering and absorption mechanisms in biological tissues, e.g., in a blood vessel (coronary artery), an esophagus, and skin, respectively.

In biological tissues, scattering and absorption mechanisms can predominate. For example, FIG. 12 shows a schematic of the boundaries of the regions of atherosclerotic plaque in a vessel. Certain embodiments of phantoms can include rendered regions of any arterial tissue, e.g., including but not limited to those in the tunica intima, tunica media, and/or tunica adventitia. In tissue analogs and phantoms, the scattering mechanisms can be approximated in, for example, optically transmissive media like glass or polymer media through a number of different processes. Some examples include surface processing and texturing through roughening, abrasion, molding, or embedding scattering elements. Other examples include bulk processing that can include both scattering and absorption, including irradiation (producing color centers), molding with or otherwise forming layers and introducing dye mixtures, chemical treatments, and/or other processes. For OCT, a single scatter model can be emulated in tissue phantoms by $R(z)=I_o\alpha(z)\exp(-2\mu_t z)$, where $R(z)$ is the reflected intensity of light as a function of depth, $I_o$ is the optical power launched into the tissue, $\alpha(z)$ is the reflectivity of the tissue at depth z, and $\mu_t$ is the total attenuation coefficient composed of both the scattering and absorption coefficients. Although the absolute indices of refraction of the tissues can be emulated in the model, in certain embodiments, the absolute indices of refraction of the tissues do not have to be reproduced. Layering or adhering different layers, possibly having different optical properties such as index of refraction, scattering coefficients, birefringence, etc., can also be used.

Figure 13:
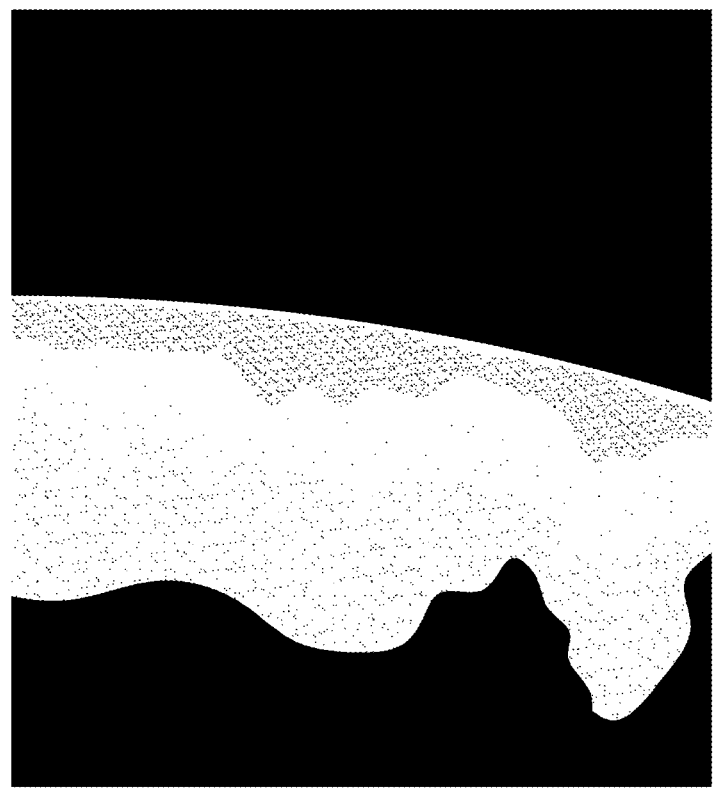
Figure 14:
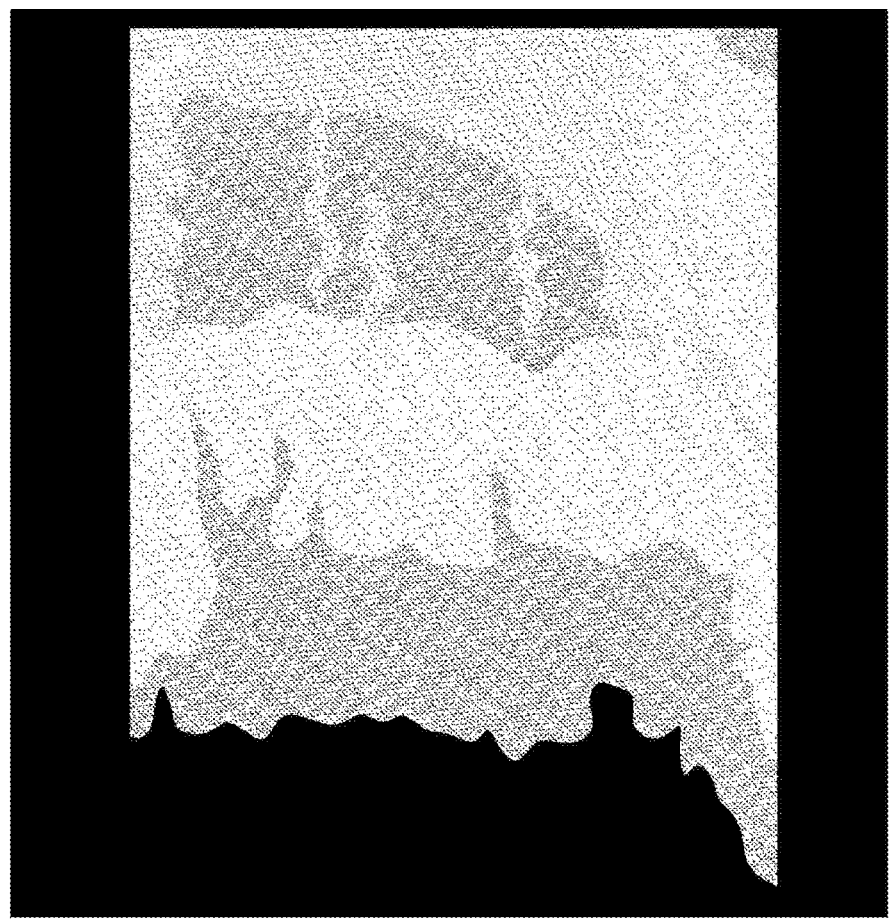

FIGS. 13-14 show additional example schematics of scattering and absorption mechanisms in biological tissues. FIG. 13 shows a distinct boundary in the esophagus composed of different tissue types with different $\mu_t$. Certain embodiments of phantoms can include rendered regions of any esophageal tissue, e.g., including but not limited to those in the mucosa (e.g., epithelium) and/or submucosa. FIG. 14 shows distinct layers in the skin where a polymer media can be configured to replicate the Δn and $\mu_{s,a}$. The rendered tissue layers of certain phantoms can include, for example, those in the epidermis, dermis, and/or subcutaneous tissue layers. Thus, beyond ophthalmology, there are many applications that exist, e.g., in areas such as dentistry, gastroenterology, gynecology, neurology, oncology, otolaryngology, pulmonology, urology, and tissues relating thereto. Certain embodiments of non-ophthalmic phantoms can include any of the features and methods of manufacture to create those features (e.g., layers) as described herein in connection with ophthalmic phantoms.

In any sort of biological tissue where there are layers, it is possible to build an optical phantom or analog. This will likely be a help to clinicians or researchers to check their instruments when the biological tissue is not present, or when the effect is so transitory it is difficult to capture. Thus, it is possible to build tissue analogs of disease states that are rapidly changing, like metasizing cancerous tumors. Other applications are also possible.

The present invention has been described herein with respect to specific embodiments. Although the invention has been described with reference to these embodiments, it will be recognized that the embodiments are intended to be illustrative, and not limiting. A wide variety of variations are possible. For example, components may be added, removed, and/or rearranged. Method steps may also be added, removed, or reordered. Various features, components, and/or steps for different embodiments may be combined in a wide variety of ways. Other modifications within the scope of the invention may be readily apparent to those of skill in the art.

What is claimed is:

1. An eye model, comprising:
 a substantially solid state assembly of one or more optically transmissive media having a first portion and a second portion, the one or more optically transmissive media providing similar optical properties as that between a corneal surface and a retina of an eye;
 a rendered retina disposed in the second portion of the assembly and representative of the retina of an eye, the rendered retina having one or more volume features associated with the retina of the eye,
 wherein the one or more features comprises one or more layers associated with the rendered retina.

2. The eye model of claim 1, wherein the substantially solid state assembly comprises substantially entirely glass or polymer.

3. The eye model of claim 1, wherein the one or more optically transmissive media substantially comprises a single piece of optically transmissive material, the first portion defining the rendered corneal surface, the second portion defining the rendered retina.

4. The eye model of claim 3, wherein the single piece of transmissive material further defines a pupil stop formed by a reduction in lateral dimension along an axis extending from the rendered corneal surface to the rendered retina.

5. The eye model of claim 1, further comprising a rendered choroidal/sclera reflector.

6. The eye model of claim 1, wherein the one or more layers further comprise a feature defining a rendered foveal pit or rendered optical nerve head.

7. The eye model of claim 1, wherein at least one layer comprises nanoparticles.

8. The eye model of claim 7, wherein at least one other layer comprises a diffusion layer adjacent the nanoparticles.

9. The eye model of claim 1, wherein a difference in index of refraction between at least two adjacent layers is less than about 0.1.

10. The eye model of claim 1, wherein at least one surface of the one or more layers has surface roughness.

11. The eye model of claim 10, wherein at least one interface between at least two layers has surface roughness.

12. The eye model of claim 1, wherein at least two layers have respective optic axes with different orientations.

13. The eye model of claim 1, further comprising a rendered choroidal/sclera reflector.

14. An eye model, comprising:
 a substantially solid state assembly of one or more optically transmissive media having a first portion and a second portion, the one or more optically transmissive media providing similar optical properties as that between a corneal surface and a retina of an eye;
 a rendered retina disposed in the second portion of the assembly and representative of the retina of an eye, the rendered retina having one or more volume features associated with the retina of the eye,
 wherein the substantially solid state assembly comprises substantially entirely glass or polymer.

15. The eye model of claim 14, wherein the one or more optically transmissive media substantially comprises a single piece of optically transmissive material, the first portion defining the rendered corneal surface, the second portion defining the rendered retina.

16. The eye model of claim 14, wherein the single piece of transmissive material further defines a pupil stop formed by a reduction in lateral dimension along an axis extending from the rendered corneal surface to the rendered retina.

17. The eye model of Claim 14, further comprising a rendered choroidal/sclera reflector.

* * * * *